United States Patent [19]

Murase et al.

[11] Patent Number: 5,413,683
[45] Date of Patent: May 9, 1995

[54] OXYGEN SENSING APPARATUS AND METHOD USING ELECTROCHEMICAL OXYGEN PUMPING ACTION TO PROVIDE REFERENCE GAS

[75] Inventors: Takao Murase, Konan; Motohiro Nishiwaki, Nagoya, both of Japan

[73] Assignee: NGK Insulators Ltd., Japan

[21] Appl. No.: 199,638

[22] Filed: Feb. 22, 1994

[30] Foreign Application Priority Data

Mar. 25, 1993 [JP] Japan ................. 5-091954
Mar. 26, 1993 [JP] Japan ................. 5-092067

[51] Int. Cl.⁶ ........................................ G01N 27/26
[52] U.S. Cl. ........................ 204/183.16; 204/425; 204/426; 204/427; 204/429; 204/153.18
[58] Field of Search ............... 204/425, 426, 427, 412, 204/428, 429, 153.16, 153.18

[56] References Cited

U.S. PATENT DOCUMENTS 4,272,329 6/1981 Hetrick et al. .................. 204/425
4,765,880 8/1988 Hayakawa et al. ............. 204/425

FOREIGN PATENT DOCUMENTS

0218357 4/1987 European Pat. Off. .
2083629 3/1982 United Kingdom .

*Primary Examiner*—John Niebling
*Assistant Examiner*—Bruce F. Bell
*Attorney, Agent, or Firm*—Parkhurst, Wendel & Rossi

[57] ABSTRACT

An oxygen sensing apparatus for detecting an oxygen concentration of a gas is disclosed. The apparatus includes a first electrochemical cell having an oxygen-ion conductive solid electrolyte body and a reference and a measuring electrode, for producing an electromotive force which corresponds to the oxygen concentration of the gas. A reference-gas chamber formed around the reference electrode is provided with a reference gas by an oxygen pumping action of the first electrochemical cell. The apparatus further includes a second electrochemical cell including a solid electrolyte body and a pair of electrodes, one disposed in a measurement-gas chamber formed around the measuring electrode, and the other exposed in an external space. The measurement-gas chamber is provided with an oxygen gas by an oxygen pumping action of the second electrochemical cell to feed oxygen from the external space into the measurement-gas chamber. Also disclosed is a method of detecting an oxygen concentration using the above-described apparatus.

10 Claims, 7 Drawing Sheets

OXYGEN SENSING APPARATUS AND METHOD USING ELECTROCHEMICAL OXYGEN PUMPING ACTION TO PROVIDE REFERENCE GAS

BACKGROUND OF THE INVENTION

1. Field of the Invention

The present invention relates to an oxygen sensing apparatus which operates according to the principle of an oxygen concentration cell, and an oxygen sensing method using this apparatus. More particularly, this invention is concerned with such an oxygen sensing apparatus that is capable of detecting a wide range of oxygen concentration of the measurement gas with high accuracy and/or improved operating response, and such a detecting method using this apparatus.

2. Discussion of the Related Art

As an apparatus for detecting an oxygen concentration of combustion exhaust gases such as those emitted by internal combustion engines of automobiles or various industrial furnaces to determine an air/fuel (A/F) ratio of an air-fuel mixture supplied to the engines or industrial furnaces, there is known an oxygen sensing apparatus which operates according to the principle of an oxygen concentration cell. The oxygen sensing apparatus has an electrochemical cell which consists of an oxygen-ion conductive solid electrolyte body, a reference electrode exposed to a reference gas, and a measuring electrode exposed to a measurement gas to be measured by the apparatus. In operation, an electromotive force is induced between the reference electrode and the measuring electrode, due to a difference in the oxygen concentration between the reference gas and the measurement gas, according to the principle of an oxygen concentration cell.

While the atmosphere may be used as the reference gas for the oxygen sensing apparatus of the above type, the apparatus may produce by itself a reference gas having a relatively high concentration of oxygen, by applying a comparatively small amount of current between the reference electrode and the measuring electrode, to thereby cause the electrochemical cell to effect an oxygen pumping action for supplying a reference-gas chamber with the reference gas.

In the oxygen sensing apparatus of the above type adapted to produce the reference gas by itself, however, the electromotive force (the output of the apparatus) generated by the electrochemical cell is remarkably increased as the oxygen concentration of the measurement gas is lowered, whereby the electromotive force no longer accurately reflects or represents the oxygen concentration of the measurement gas, causing a considerably large measuring error in the output of the apparatus. This may be because the surface of the measuring electrode suffers from lack or insufficiency of oxygen due to the oxygen pumping action of the electrochemical cell when the oxygen concentration of the measurement gas is low.

In this regard, it is considerably difficult to compensate or rectify the apparatus output to remove the measuring error which occurs upon measurement of low-oxygen-concentration measurement gases since the amount of such measuring error greatly varies depending upon the oxygen concentration of the gas. Accordingly, the measurement gas having a relatively low concentration of oxygen cannot be accurately measured by the oxygen sensing apparatus of the above known type wherein the reference gas is produced by its oxygen pumping action.

The measuring error as described above can be effectively reduced by reducing the current applied between the reference electrode and measuring electrode, so as to permit accurate measurement of oxygen concentration in a relatively low range. However, the reduction of the current results in considerable deterioration of the operating response of the sensing apparatus with respect to the measurement gas having a relatively high concentration of oxygen.

SUMMARY OF THE INVENTION

It is therefore a first object of the present invention to provide an oxygen sensing apparatus of an oxygen concentration cell type, which produces a reference gas by an oxygen pumping action of its electrochemical cell, and which is capable of detecting a wide range of oxygen concentration of a measurement gas with high accuracy, with a significantly reduced error upon measurement of the measurement gas having a relatively low concentration of oxygen, and preferably with high operating response.

It is a second object of the invention to provide a method of detecting the oxygen concentration of a gas, which uses the oxygen sensing apparatus as described above.

The first object may be attained according to one aspect of the present invention, which provides an oxygen sensing apparatus for detecting an oxygen concentration of a measurement gas, comprising: a first electrochemical cell including a first oxygen-ion conductive solid electrolyte body, a reference electrode exposed to a reference gas having a predetermined high concentration of oxygen, and a measuring electrode exposed to the measurement gas, the reference electrode and the measuring electrode being formed on the solid electrolyte body, the first electrochemical cell producing an electromotive force corresponding to the oxygen concentration of the measurement gas, the electromotive force being induced between the reference electrode and the measuring electrode due to a difference in the oxygen concentration between the measurement gas and the reference gas; means for defining a reference-gas chamber formed around the reference electrode, the reference-gas chamber being provided with the reference gas by an oxygen pumping action effected with a small amount of current being applied between the reference electrode and the measuring electrode so as to effect an oxygen pumping action of the first electrochemical cell; means for defining a measurement-gas chamber formed around the measuring electrode, the measurement gas being introduced into the measurement-gas chamber; and a second electrochemical cell including a second oxygen-ion conductive solid electrolyte body and a pair of electrodes, one of the pair of electrodes being disposed in the measurement-gas chamber while the other of the pair of electrodes being exposed in an external gas space outside the apparatus, the second electrochemical cell performing an oxygen pumping action so as to feed an oxygen gas from the external gas space into the measurement-gas chamber.

When the oxygen concentration of a measurement gas is detected by the oxygen sensing apparatus constructed as described above, an oxygen gas is fed from the measurement-gas chamber into the reference-gas chamber under the oxygen pumping action of the first electrochemical cell, while an oxygen gas is fed from the external gas space into the measurement-gas chamber under the oxygen pumping action of the second electrochemical cell.

By controlling the amount of the oxygen gas supplied to the measurement-gas chamber by the second electrochemical cell, the present oxygen sensing apparatus can avoid lack or insufficiency of oxygen around the measuring electrode disposed in the measurement-gas chamber even if the measurement gas has a relatively low concentration of oxygen. Further, the oxygen concentration of the measurement gas can be accurately reflected or represented by the electromotive force (the output of the apparatus) produced by the first electrochemical cell, even if the oxygen concentration varies over a large range.

Accordingly, the relationship based on the Nernst's equation can be favorably maintained between the oxygen concentration of the measurement gas and the output of the apparatus, that is, the value of the electromotive force, by controlling the amount of the oxygen gas supplied to the measurement-gas chamber by the second electrochemical cell, in other words, by suitably controlling the level of the electric current to be applied to the electrodes of the second electrochemical cell. Thus, the present oxygen sensing apparatus is capable of detecting the oxygen concentration of a gas with high detecting accuracy, over a sufficiently wide range.

The second object of the present invention may be attained according to a second aspect of the invention, which provides a method of detecting an oxygen concentration of a measurement gas by using the oxygen sensing apparatus as described just above, the method comprising the steps of (a) detecting the electromotive force induced between the reference electrode and the measuring electrode of the first electrochemical cell, and (b) determining an amount of a current applied between the pair of electrodes of the second electrochemical cell for effecting the oxygen pumping action, so that the electromotive force is proportional to a natural logarithm of the oxygen concentration of the measurement gas introduced into the measurement-gas chamber.

According to the method of the present invention as described above, the second electrochemical cell performs an oxygen pumping action for feeding an oxygen gas from the external gas space into the measurement-gas chamber, by an amount corresponding to that of an oxygen gas which is pumped from the measurement-gas chamber into the reference-gas chamber under the oxygen pumping action of the first electrochemical cell. This method can prevent any possible influence caused by the oxygen pumping action of the first electrochemical cell.

Accordingly, the present method makes it possible to avoid lack or shortage of oxygen around the measuring electrode due to the oxygen pumping action of the first electrochemical cell even when the measurement gas has a relatively low concentration of oxygen. Consequently, the relationship based on the Nernst's equation can be favorably maintained between the oxygen concentration of the measurement gas and the output of the apparatus (electromotive force generated by the first electrochemical cell) even if the concentration is changed from a relatively low range to a relatively high range, assuring a sufficiently high accuracy of detection of the oxygen concentration of the measurement gas over a wide range.

The above-indicated first object of the invention may be also attained according to a third aspect of the invention, which provides an oxygen sensing apparatus for detecting an oxygen concentration of a measurement gas, comprising: an electrochemical cell including an oxygen-ion conductive solid electrolyte body, a reference electrode exposed to a reference gas having a predetermined high concentration of oxygen, and a measuring electrode exposed to the measurement gas, the reference electrode and the measuring electrode being formed on the solid electrolyte body, the electrochemical cell producing an electromotive force which corresponds to the oxygen concentration of the measurement gas, the electromotive force being induced between the reference electrode and the measuring electrode due to a difference in the oxygen concentration between the measurement gas and the reference gas; means for defining a reference-gas chamber formed around the reference electrode, the reference-gas chamber being provided with the reference gas by an oxygen pumping action effected with a small amount of current being applied between the reference electrode and the measuring electrode; a power source for applying a current between the reference electrode and the measuring electrode, so as to effect the oxygen pumping action to provide the reference gas in the reference-gas chamber; and switching means for increasing an amount of current to be supplied by the power source, with an increase in an expected maximum value of the oxygen concentration of the measurement gas, which expected maximum value defines an upper limit of a measurement range within which the oxygen concentration is determined from the electromotive force.

The above-indicated second object may also be attained according to a fourth aspect of the invention, which provides a method of detecting an oxygen concentration of a measurement gas, by using an oxygen sensing apparatus including an electrochemical cell having an oxygen-ion conductive solid electrolyte body, a reference electrode exposed to a reference gas having a predetermined high concentration of oxygen, a measuring electrode exposed to the measurement gas, and a reference-gas chamber formed around the reference electrode, the reference electrode and the measuring electrode being formed on the solid electrolyte body, the method including the steps of: (a) applying a small amount of current between the reference electrode and the measuring electrode to effect an oxygen pumping action, so as to provide the reference gas in the reference-gas chamber; (b) detecting an electromotive force induced between the reference electrode and the measuring electrode of the electrochemical cell, as an output signal representative of the oxygen concentration of the measurement gas; and (c) increasing an amount of the current to be applied between the reference electrode and the measuring electrode, with an increase in an expected maximum value of the oxygen concentration of the measurement gas, which expected maximum value defines an upper limit of a measurement range within which the oxygen concentration is determined from the electromotive force.

According to the third and fourth aspects of the invention, the amount of the current to be applied between the reference electrode and the measuring electrode is controlled or changed depending upon the expected maximum value of the oxygen concentration of the measurement gas. More specifically, the current is set at a relatively small value for the measurement gas whose oxygen concentration is relatively low, with a result of a significantly reduced measuring error for such measurement gas, while the current is set at a relatively large value for the measurement gas whose oxygen concentration is relatively high, thus assuring an excellent operating response of the apparatus for such measurement gas.

In one preferred form of the fourth aspect of the invention, the current to be applied between the reference electrode and the measuring electrode is held in a range defined by a lower limit $I_{min}$ ($\mu A$) as represented by the formula $I_{min}$ ($\mu A$)=0.1 log[O$_2$max]+0.1, and an upper limit $I_{max}$ ($\mu A$) as represented by the formula Imax ($\mu A$)=5 log[O$_2$max]+1, where O$_2$max (ppm) is the expected maximum value of the oxygen concentration of the measurement gas. With the current held in the above range, a low-oxygen-concentration gas can be measured with further improved measuring accuracy, and a high-oxygen-concentration gas can be measured with a further improved operating response.

BRIEF DESCRIPTION OF THE DRAWINGS

The above and optional objects, features and advantages of the present invention will be better understood by reading the following detailed description of presently preferred embodiments of the invention, when considered in connection with the accompanying drawings, in which:

FIG. 7(a) is a graph indicating a change in the electromotive force produced by the electrochemical cell of the apparatus of FIG. 4, with the oxygen concentration of the measurement gas, when the current applied to the cell is 5 $\mu A$, while

DETAILED DESCRIPTION OF THE PREFERRED EMBODIMENTS

Figure 1:
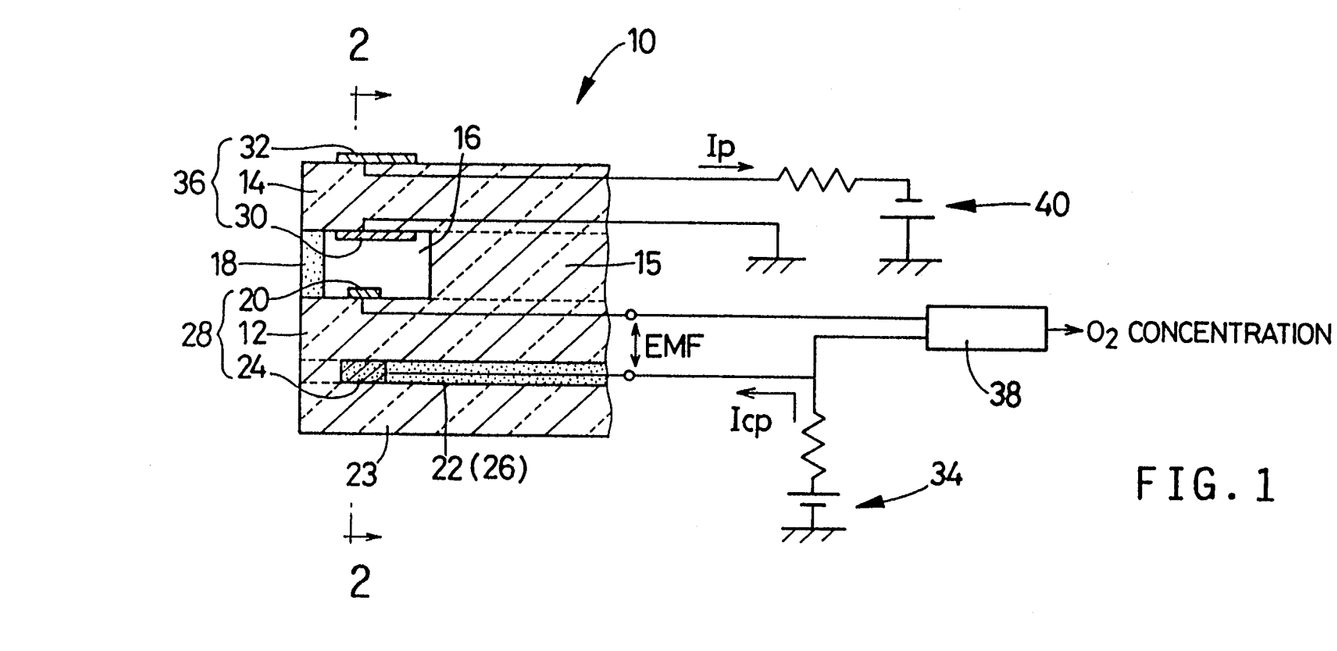
FIG. 1 is a schematic elevational view in longitudinal cross section of one embodiment of an oxygen sensing apparatus of the present invention.
Figure 2:
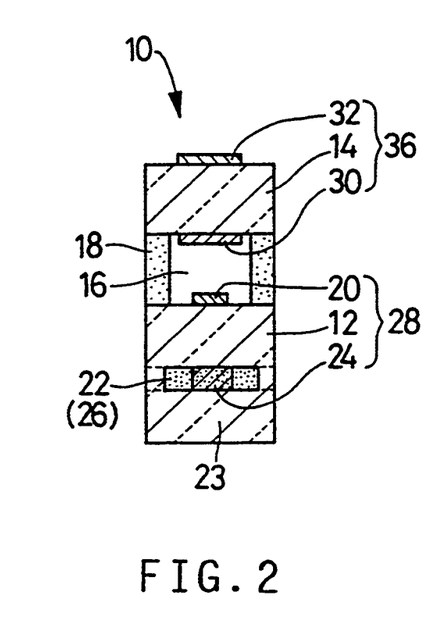
FIG. 2 is a transverse cross sectional view of the oxygen sensing apparatus taken along line 2—2 of FIG. 1.

Referring first to FIGS. 1 and 2, there is shown one preferred embodiment of the present invention in the form of an oxygen sensing apparatus 10, which has a laminar structure including a first solid electrolyte layer 12 and a second solid electrolyte layer 14 that are formed of an oxygen-ion conductive ceramic material such as zirconia.

Spacer layer 15 is interposed between the first and second solid electrolyte layers 12, 14, to cooperate with the layers 12, 14 to define a flat measurement-gas chamber 16 into which a measurement gas to be dealt with the apparatus 10 is introduced. In this embodiment, a porous ceramic plug 18 is provided at an open end of the measurement-gas chamber 16, so that the measurement gas is introduced into the chamber 16 through the porous ceramic plug 18.

Measuring electrode 20 made of platinum, for example, is formed on the first solid electrolyte layer 12, such that the electrode 20 is exposed to the measurement-gas chamber 16 as described above.

On the lower surface of the first solid electrolyte layer 12 remote from the measuring electrode 20, there is formed a porous solid electrolyte layer 22 made of an oxygen-ion conductive ceramic material such as zirconia. Further, a gastight ceramic layer 23 is formed in contact with the lower surface of the porous solid electrolyte layer 22 remote from the first solid electrolyte layer 12.

Further, a reference electrode 24 made of platinum, for example, is formed in a portion of the porous solid electrolyte layer 22. That is, the reference electrode 24 is formed with a porous structure, and is connected to the first solid electrolyte layer 12. Thus, a reference-gas chamber 26 is provided by the porous solid electrolyte layer 22, so that the reference electrode 24 is exposed to the chamber 26.

In the instant embodiment, the first solid electrolyte layer 12, measuring electrode 20 and reference electrode 24 constitute a first electrochemical cell 28 for producing an electromotive force corresponding to the oxygen concentration of the measurement gas, as described below.

On the other hand, an inner electrode 30 made of platinum, for example, is formed on the second solid electrolyte layer 14, such that the electrode 30 is exposed to the measurement-gas chamber 16. This inner electrode 30 is disposed close to the measuring electrode 20 within the measurement-gas chamber 16, such that these two electrodes 30, 20 are opposed to each other in the direction of the thickness of the solid electrolyte layers 12, 14.

Further, an outer electrode 32 made of platinum, for example, is formed on the surface of the second solid electrolyte layer 14 which is exposed to an external space, such that the electrode 32 is exposed to a measurement gas or the atmosphere that exists in the external space.

In the instant embodiment, the second solid electrolyte layer 14, inner electrode 30, and outer electrode 32 constitute a second electrochemical cell 36 for performing an oxygen pumping action as described below.

In the thus constructed oxygen sensing apparatus 10, a first DC power source 34 for producing the reference gas is connected between the measuring electrode 20 and reference electrode 24 of the first electrochemical cell 28, so that a predetermined small amount of electric current Icp is applied to the cell 28 in a direction from the reference electrode 24 to the measuring electrode 20. As a result, the first electrochemical cell 28 performs an oxygen pumping action to move an oxygen gas from the measurement-gas chamber 16 to the reference-gas chamber 26 through the first solid electrolyte layer 12. The oxygen gas, which is kept in the chamber 26, serves as a reference gas having a relatively high oxygen concentration and acting on the reference electrode 24. The oxygen concentration in the reference-gas chamber 26 is maintained at a given value which is determined depending on the level of the minute current Icp applied between the measuring electrode 20 and the reference electrode 24, once the amount of the oxygen gas pumped into the chamber 26 is brought into equilibrium with the amount of the oxygen gas discharged from the chamber 26 into the external space through the porous solid electrolyte layer 22.

With the reference electrode 24 exposed to the high-oxygen-concentration reference gas present in the reference-gas chamber 26, an electromotive force EMF is induced between the reference electrode 24 and the measuring electrode 20, due to a difference in oxygen concentration between the measurement gas to which the measuring electrode 20 is exposed, and the reference gas in the chamber 26. This electromotive force EMF is fed to an electronic circuit 38, which calculates an oxygen concentration level of the measurement gas based on the received electromotive force EMF, according to the Nernst's equation known in the art. The circuit 38 produces an output representative of the calculated oxygen concentration of the measurement gas.

The instant oxygen sensing apparatus 10 further includes a second DC power source 40 which is connected between the inner and outer electrodes 30, 32 of the second electrochemical cell 36, so that a predetermined small current Ip is applied to the cell 36 in a direction from the inner electrode 30 toward the outer electrode 32. This second electrochemical cell 28 performs an oxygen pumping action to feed an oxygen gas from the external space into the measurement-gas chamber 16.

In the oxygen sensing apparatus 10 constructed as described above, an oxygen gas is supplied from the measurement-gas chamber 16 to the reference-gas chamber 26, under the oxygen pumping action of the first electrochemical cell 28, so as to produce the high-oxygen-concentration reference gas in the reference-gas chamber 26. At the same time, an oxygen gas is fed from the external space to the measurement-gas chamber 16, under the oxygen pumping action of the second electrochemical cell 36, so as to compensate for an amount of the oxygen supplied from the chamber 16 to the reference-gas chamber 26.

It will be understood from the above description that the instant oxygen sensing apparatus 10 utilizes the oxygen pumping action of the second electrochemical cell 36 for reducing or eliminating an influence of a supply of the oxygen gas from the measurement-gas chamber 16 to the reference gas chamber 26 under the oxygen pumping action performed by the first electrochemical cell 28. Accordingly, the present apparatus 10 can avoid lack or shortage of oxygen around the measuring electrode 20 due to the oxygen pumping action of the first electrochemical cell 26, even when the oxygen concentration of the measurement gas is comparatively low. In this case, the apparatus 10 does not suffer from a considerable degree of reduction in its measuring accuracy, which would otherwise occur due to the lack of oxygen around the electrode 20. Thus, the instant oxygen sensing apparatus 10 is capable of detecting the oxygen concentration of the measurement gas with sufficiently high accuracy, over a comparatively wide range of the oxygen concentration.

Since the open end portion of the measurement-gas chamber 16 otherwise open to the external space is filled with the porous ceramic plug 18 in the instant embodiment, the oxygen gas supplied to the chamber 16 due to the oxygen pumping action of the second electrochemical cell 36 is advantageously retained or kept in the measurement-gas chamber 16, and can be efficiently brought into contact with the measuring electrode 20.

The amount of the current Ip to be applied from the second DC power source 40 between the inner and outer electrodes 32 of the second electrochemical cell 36 is desirably determined such that the electromotive force EMF induced by the first electrochemical cell 28 is directly proportional to the natural logarithm of the oxygen concentration of the measurement gas that is being measured. The application of the thus determined current Ip effectively reduces an error in the oxygen concentration of the measurement gas which is calculated according to the Nernst's equation, based on the value of the electromotive force EMF generated by the first electrochemical cell 28.

The current value Ip which satisfies the above-described relationship varies depending upon various factors, such as the structure of the measurement-gas chamber 16, a diffusion resistance under which the measurement gas is diffused through the porous plug 18 into the measurement-gas cheer 16, and the positional relationship between the measuring electrode 20 and inner electrode 30 in the measurement-gas chamber 16. While an appropriate current value Ip can be actually obtained or determined by using a calibration gas or test gas, for each specific sensing element having the first and second electrochemical cells 28, 36, the current value Ip is generally determined so that the current Ip is equal to the current Icp supplied from the first DC power source 34 between the measuring electrode 20 and reference electrode 24 of the first electrochemical cell 28.

If the current Ip applied between the inner and outer electrodes 30, 32 is determined to be equal to the current Icp applied between the measuring and reference electrodes 20, 24, as described above, the determination of the current Ip supplied by the second DC power source 40 can be considerably simplified. Another advantage according to this determination is that the second electrochemical cell 36 can satisfactorily compensate for the amount of the oxygen gas that is discharged from the measurement-gas chamber 16 due to the pumping action of the first electrochemical cell 28, whereby an influence of the oxygen pumping action of the first electrochemical cell 28 on the output characteristic of the sensing apparatus 10 can be effectively eliminated.

The output characteristic of the electrochemical cell 28 of the oxygen sensing apparatus 10 of the instant embodiment was actually measured using a calibrating gas having known concentrations of components, when a small current Icp of 3 $\mu$A was applied between the measuring electrode 20 and the reference electrode 24, while a current Ip applied between the inner electrode 30 and the outer electrodes 30, 32 was set at each of four values 0 $\mu$A, 1 $\mu$A, 3 $\mu$A and 5 $\mu$A. The results of the measurements are indicated in the graph of FIG. 3.

Figure 3:
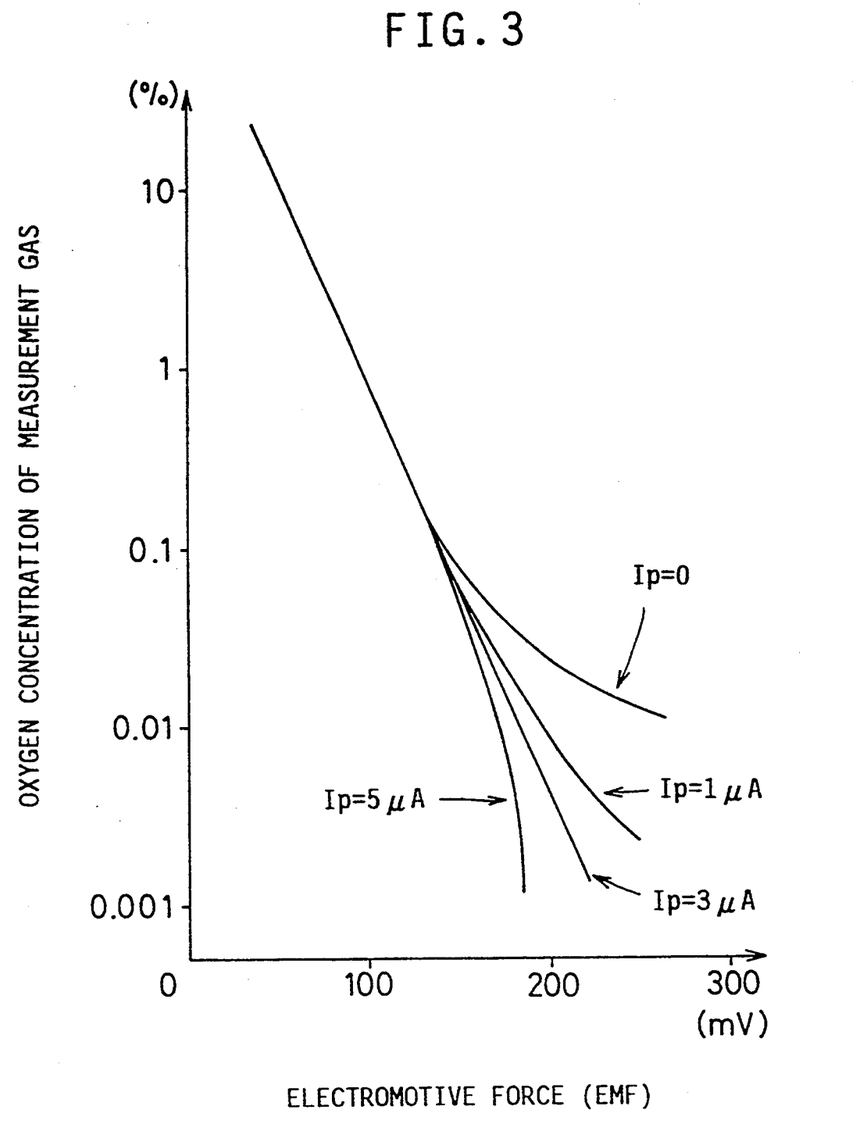
FIG. 3 is a graph indicating the relationship between the electromotive force (EMF) produced by a first electrochemical cell of the apparatus and the oxygen concentration of the measurement gas.

It will be understood from the results indicated in FIG. 3 that the linearly proportional relationship between the oxygen concentration of the measurement gas as represented by Nernst's equation and the output (detected electromotive force EMF) of the cell 28 can be effectively improved by applying a small amount of current Ip between the inner electrode 30 and the outer electrode 32, when the oxygen concentration of the measurement gas is in a comparatively low range. Thus, the proportional relationship between the actual oxygen concentration and the produced EMF can be made highly linear over a considerably wide range of oxygen concentration of the measurement gas. It will also be understood that this effect is most conspicuous when the current Ip applied between the inner and outer electrodes 30, 32 is 3 µA, that is, is equal to the current Icp applied between the measuring electrode 20 and the reference electrode 24.

Figure 4:
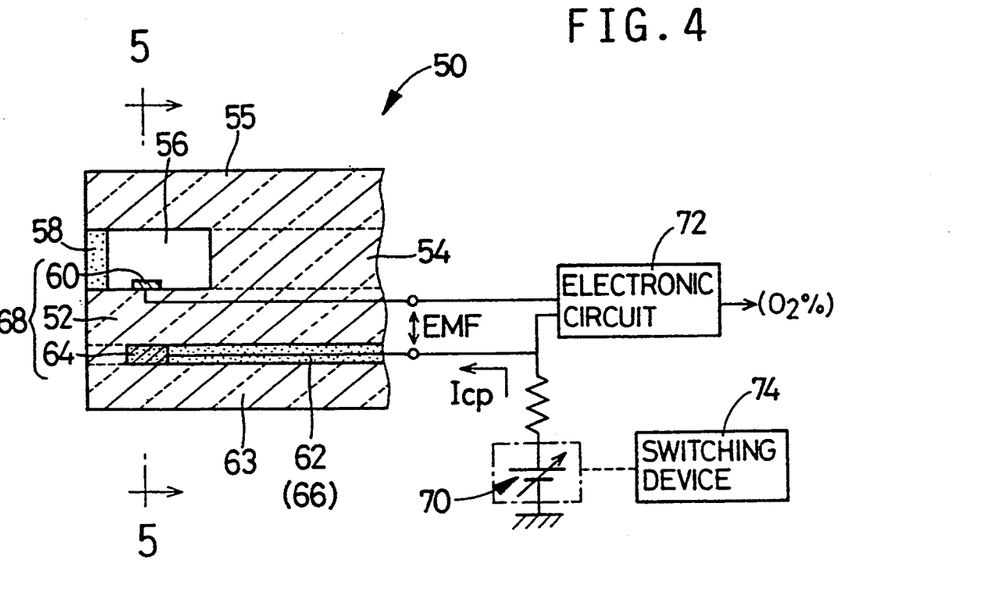
FIG. 4 is a schematic elevational view in longitudinal cross section of another embodiment of an oxygen sensing apparatus of the present invention.
Figure 5:
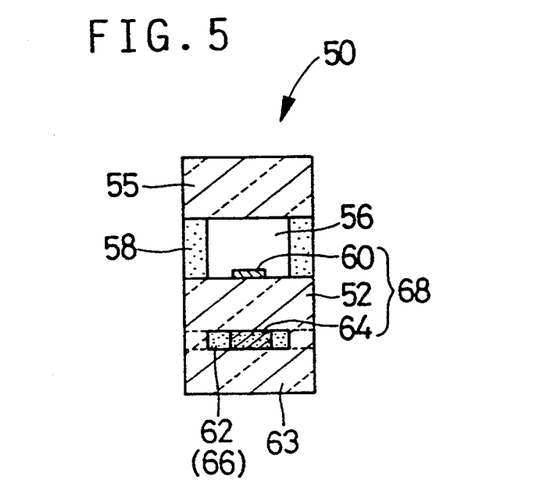
FIG. 5 is a cross sectional view taken along line 5—5 of FIG. 4.

Referring next to FIG. 4 and 5, there is shown another preferred embodiment of the present invention in the form of an oxygen sensing apparatus 50, which has a laminar structure including a solid electrolyte layer 52 formed of an oxygen-ion conductive ceramic material such as zirconia.

Spacer layer 54 is formed on the solid electrolyte layer 52, and gastight upper ceramic layer 55 is formed on the spacer layer 54, so as to provide a laminar structure 52, 54, 55. Between the solid electrolyte layer 52 and the upper ceramic layer 55, there is formed a flat measurement-gas chamber 56 into which a measurement gas to be dealt with by the apparatus 50 is introduced. In the instant embodiment, a porous ceramic plug 58 is provided at an open end of the measurement-gas chamber 56, so that the gas to be measured is introduced into the chamber 56 through the porous ceramic plug 58.

Measuring electrode 60 made of platinum, for example, is formed on the solid electrolyte layer 52, such that the electrode 60 is exposed to the measurement-gas chamber 56 as described above.

On the lower surface of the solid electrolyte layer 52 remote from the measuring electrode 60, there is formed a porous solid electrolyte layer 62 made of an oxygen-ion conductive ceramic material such as zirconia. Further, a gastight lower ceramic layer 63 is formed in contact with the lower surface of the porous solid electrolyte layer 62 remote from the solid electrolyte layer 52, so as to provide a laminar structure 52, 62 and 63.

Further, reference electrode 64 made of platinum, for example, is formed in a portion of the porous solid electrolyte layer 62, such that the electrode 64 is in contact with the lower surface of the solid electrolyte layer 52. That is, the reference electrode 64 has a porous structure, and is connected to the solid electrolyte layer 52. In this arrangement, a reference-gas chamber 66 is provided by the porous solid electrolyte layer 62, such that the porous reference electrode 64 is exposed to the chamber 66.

In the instant embodiment, the solid electrolyte layer 52, measuring electrode 60 and reference electrode 64 constitute an electrochemical cell 68 for producing an electromotive force corresponding to the oxygen concentration of the measurement gas that is being measured.

In the thus constructed oxygen sensing apparatus 50, a DC power source 70 for producing a reference gas is connected between the measuring electrode 60 and reference electrode 64 of the electrochemical cell 68, so that a predetermined small amount of current Icp is applied to the cell 68 in a direction from the reference electrode 64 to the measuring electrode 60. In this manner, the electrochemical cell 68 performs an oxygen pumping action to move an oxygen gas from the measurement-gas chamber 56 to the reference-gas chamber 66. The oxygen gas, which is kept in the reference-gas chamber 66, serves as a reference gas having a relatively high oxygen concentration, which acts on the reference electrode 64. The oxygen concentration in the reference-gas chamber 66 is maintained at a given value which is determined depending on the value of the current Icp applied between the measuring electrode 60 and the reference electrode 64, once the amount of the oxygen gas pumped into the chamber 66 is brought into equilibrium with the amount of an oxygen gas that is discharged from the chamber 66 into the external space through the porous solid electrolyte layer 62.

With the reference electrode 64 exposed to the high-oxygen-concentration reference gas present in the reference-gas chamber 66, an electromotive force EMF is induced between the reference electrode 64 and the measuring electrode 60, due to a difference in oxygen concentration between the measurement gas to which the measuring electrode 60 is exposed, and the reference gas in the chamber 66. An electronic circuit 72 receives an input signal in the form of the electromotive force EMF, and calculates an oxygen concentration $O_2$% of the measurement gas based on the detected electromotive force EMF, according to the Nernst's equation known in the art, and produces an output indicative of the calculated $O_2$% value.

The electronic circuit 72 described above is designed to change an amplification factor for amplifying the output signal (the electromotive force EMF) of the electrochemical cell 68, so that the presently established amplification factor corresponds to the range in which the oxygen concentration of the measurement gas is expected to vary.

The DC power source 70 for producing the reference gas is a variable power source whose voltage or resistance is variable, and is connected to a switching device 74 for changing the current Icp to be supplied by the power source 70. Namely, the DC power source 70 is adapted to apply a selected one of different amounts of current Icp between the reference electrode 64 and the measuring electrode 60, depending upon the selected position of the switching device 74. When the oxygen concentration of the measurement gas is changed from one range to another, the amount of current Icp supplied by the DC power source 70 is changed from the currently selected one to another.

Namely, the current supplied by the DC power source 70 is controlled by the switching device 74 so that the current Icp applied between the reference electrode 64 and the measuring electrode 60 increases with an increase in the expected maximum value of the oxygen concentration of the measurement gas to be measured.

In the oxygen sensing apparatus 50 constructed as described above, the current Icp applied from the DC power source 70 to the reference and measuring electrodes 64, 60 is set at a relatively small value, when the measurement gas has a relatively low concentration of oxygen, that is, when the expected maximum value of the oxygen concentration is relatively small. As a result, the amount of the oxygen gas fed from the measurement-gas cheer 56 into the reference-gas chamber under the oxygen pumping action of the electrochemical cell 68 is accordingly reduced, thus favorably avoiding lack or shortage of oxygen around the measuring electrode 60. Thus, the present apparatus 50 is less likely to suffer from erroneous measurement of the oxygen concentration, and ensures excellent oxygen sensing accuracy.

When the measurement gas has a relatively high concentration of oxygen, that is, when the expected maximum value of the oxygen concentration of the measurement gas is relatively high, the current Icp applied from the DC power source 70 to the reference and measuring electrodes 64, 60 is set at a relatively high value. Accordingly, the present apparatus 50 exhibits an excellent operating response, that is, is able to immediately detect a change of the oxygen concentration of the measurement gas and determine an amount of the change.

According to the above-described method of the present invention, the oxygen sensing apparatus 50 is capable of dealing with a considerably wide range of oxygen concentration of the measurement gas with high accuracy and excellent operating response.

The relationship between the current Icp supplied by the DC power source 70 to the reference electrode 64 and measuring electrode 60 and the output characteristic of the electrochemical cell 68 was actually detected using different calibrating gases having known components and respective known different concentrations of oxygen. The results of the measurements are indicated in the graph of FIG. 6.

Figure 6:
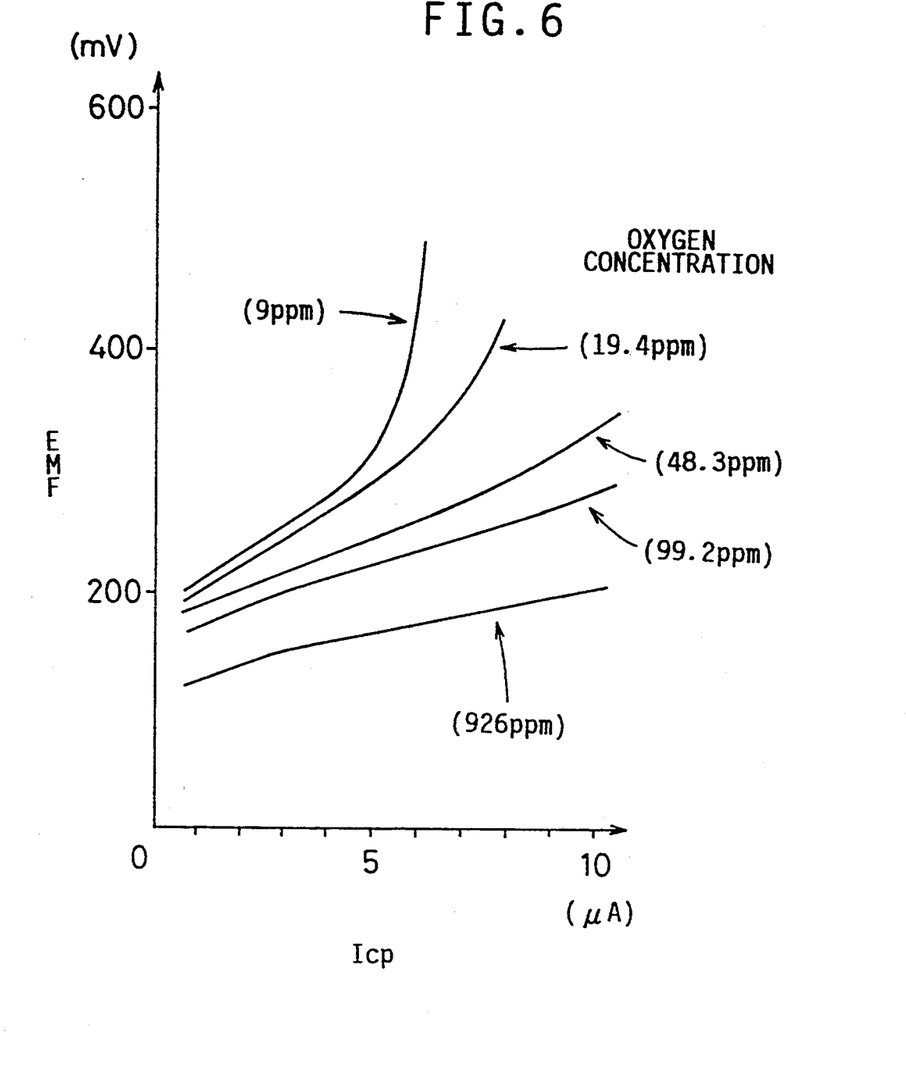
FIG. 6 is a graph indicating the relationships between a current applied to an electrochemical cell of the apparatus of FIG. 4 and an electromotive force produced by the apparatus, which relationships were obtained using gases having different oxygen concentrations.

As will be understood from the results indicated in FIG. 6, the output characteristic of the cell 68 is inevitably deteriorated with a considerably large error in the measurement result, if the current Icp is set at a large value larger than approx. 5 $\mu$A when the measurement gas has a low concentration of oxygen (e.g., 9 ppm and 19.4 ppm). Such an error can be reduced or eliminated by setting the current Icp at a small value (smaller than approx. 5 $\mu$A in this example).

The relationship between the operating response upon a change of the oxygen concentration of the measurement gas and the value of the current Icp supplied from the DC power source 70 to the reference electrode 64 and measuring electrode 60 was actually detected, using a calibrating gas having a known oxygen concentration. The results of the measurements are indicated in FIGS. 7(a) and 7(b).

Figure 7A:
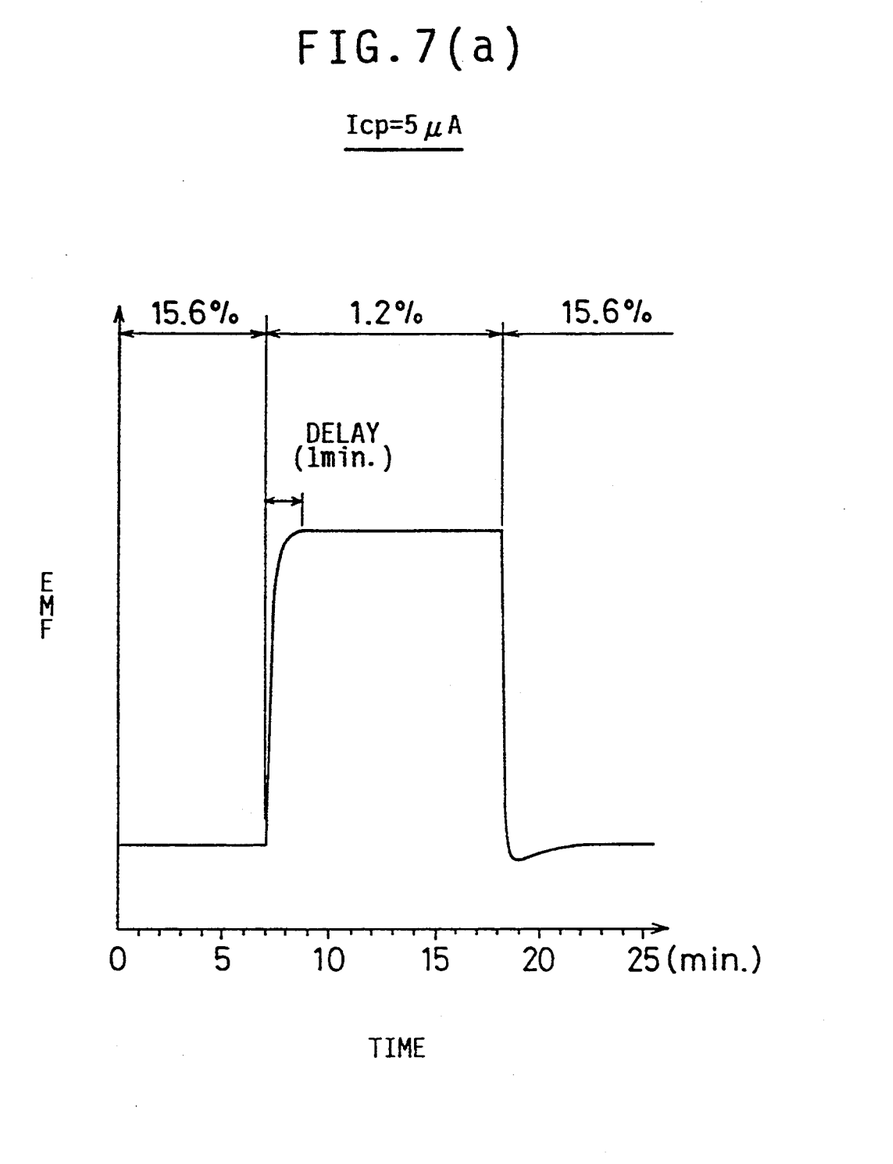
Figure 7B:
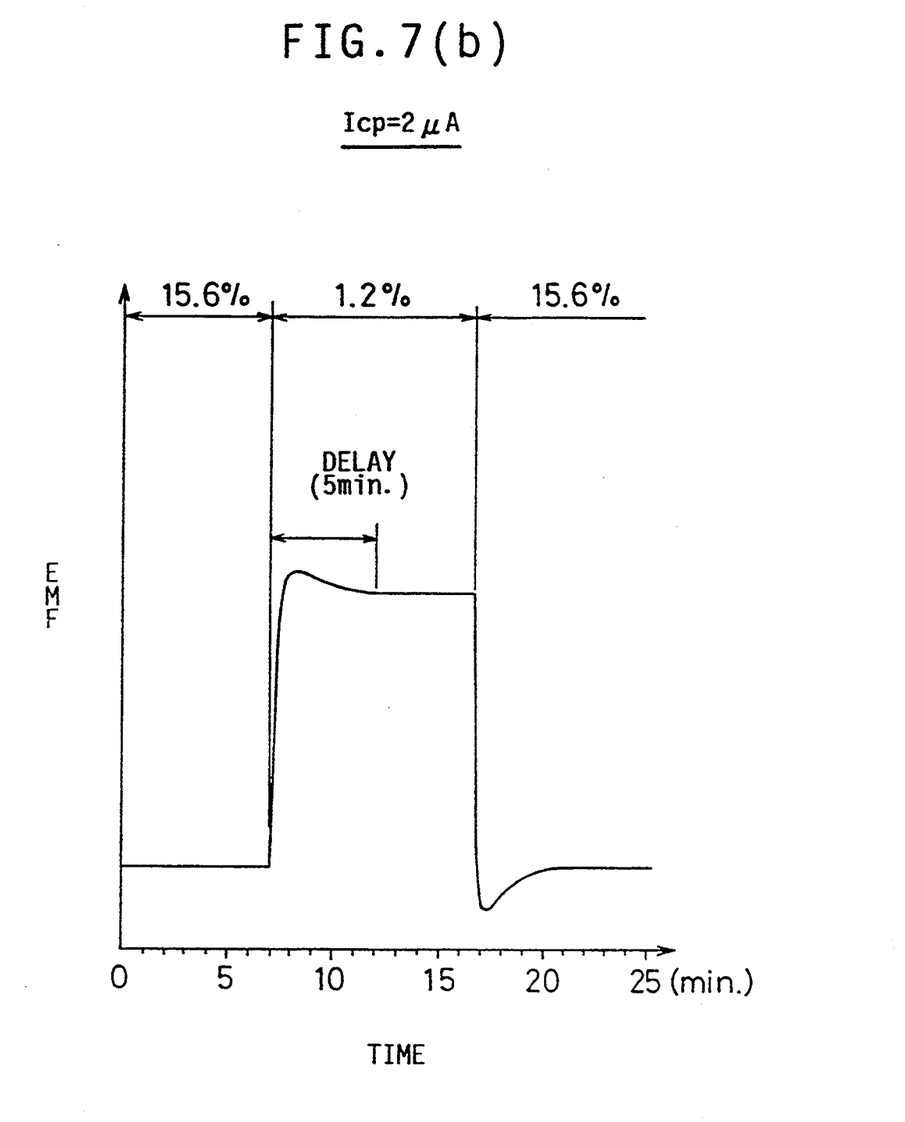
FIG. 7(b) is a graph indicating such change in the electromotive force, when the current applied to the cell is 2 $\mu A$.

It is apparent from the results indicated in FIGS. 7(a) and 7(b) that an improved operating response can be achieved by setting the current Icp at a comparatively large value (5 $\mu$A) even when the measurement gas has a high concentration of oxygen (1.2%), as compared with a response when the current Icp is set at a comparatively small value (2 $\mu$A).

As a result of numerous experiments and analyses by the inventors of the present invention, it was found that the current Icp applied from the DC power source 70 to the reference and measuring electrodes 64, 60 is preferably determined so as to satisfy the following equation (1), more preferably the following equation (2), in order to reduce sensing error with respect to a measurement gas having a low oxygen concentration while assuring an excellent operating response with respect to a measurement gas having a high oxygen concentration.

$$0.1 \log[O_2\text{max}] + 0.1 \leq I_{cp}(\mu A) \leq 5 \log[O_2\text{max}] + 1 \quad (1)$$

$$0.5 \log[O_2\text{max}] + 0.1 \leq I_{cp}(\mu A) \leq 2 \log[O_2\text{max}] + 1 \quad (2)$$

where [$O_2$max] is the expected maximum value (ppm) of the oxygen concentration of the measurement gas.

TABLE 1 shows the lower and upper limits of the current Icp which satisfy the above equation (1) and the preferable lower and upper limits of the current Icp which satisfy the above equation (2), with respect to each of seven measurement ranges of oxygen concentration of the measurement gas, which ranges are selected as indicated in TABLE 1 such that the upper limit of each range corresponds to the expected maximum oxygen concentration value (ppm) of the measurement gas.

TABLE 1

| Measurement range (ppm) | Current:Icp ($\mu$A) | | | |
|---|---|---|---|---|
| | Lower limit | Preferable lower limit | Preferable upper limit | Upper limit |
| 0~1 | 0.1 | 0.1 | 1 | 1 |
| 0~10 | 0.2 | 0.6 | 3 | 6 |
| 0~100 | 0.3 | 1.1 | 5 | 11 |
| 0~1000 | 0.4 | 1.6 | 7 | 16 |
| 0~10000 (1%) | 0.5 | 2.1 | 9 | 21 |
| 0~100000 (10%) | 0.6 | 2.6 | 11 | 26 |
| 0~1000000 (100%) | 0.7 | 3.1 | 13 | 31 |

While the presently preferred embodiments of the present invention have been described in detail, for illustrative purpose only, it is to be understood that the invention is by no means limited to the details of the illustrated embodiments, but may be otherwise embodied.

While the reference-gas chamber (26, 66) is provided by or filled with the porous solid electrolyte layer (22, 62) in the illustrated embodiments, the reference-gas cheer may be a totally vacant continuous space having a predetermined volume.

In the illustrated embodiments, the measurement gas is introduced into the measurement-gas chamber (16, 56), through the porous ceramic plug (18, 58) provided at the open end portion of the measurement-gas chamber (16, 56). However, the porous ceramic plug (18, 58) is not essential and may be eliminated.

The oxygen sensing apparatus (10, 50) may be provided with suitable heating means (not shown) as needed for holding the solid electrolyte layers (12, 14, 52) at an appropriate elevated temperature.

Further, the oxygen sensing apparatus (10, 50) may be provided with two or more measuring electrodes (20, 60), and reference electrodes (24, 64), and the apparatus (10) may also be provided with two or more inner electrodes (30) and outer electrodes (32).

In the second embodiment, the number of the measurement ranges set for the oxygen sensing apparatus 50 is not limited to any specific value but may be determined as desired. When a large number of measurement ranges are provided, the current Icp of the same value may be applied between the reference electrode and the measuring electrode, with respect to some adjacent measurement ranges whose maximum values are relatively close to each other.

It is to be understood that the present invention may be embodied with various other changes, modifications and improvements, which may occur to those skilled in the art, without departing from the spirit and scope of the invention defined by the appended claims.

What is claimed is:

1. A method of detecting an oxygen concentration of a measurement gas, comprising the steps of:
    providing an oxygen sensing apparatus comprising:
    (i) a first electrochemical cell including a first oxygen-ion conductive solid electrolyte body, a reference electrode exposed to a reference gas having a high concentration of oxygen, a measuring electrode exposed to the measurement gas, said reference electrode and said measuring electrode are formed on said solid electrolyte body, said first electrochemical cell producing an electromotive force which corresponds to the oxygen concentration of the measurement gas, said electromotive force is induced between the reference electrode and the measuring electrode due to a difference in the oxygen concentration between the measurement gas and the reference gas;

(ii) means for defining a reference-gas chamber formed around said reference electrode, said reference-gas chamber is provided with said reference gas by an oxygen pumping action effected with an amount of current ranging from about 0.1 µA to about 31 µA applied between said reference electrode and said measuring electrode;

(iii) means for defining a measurement-gas chamber formed around said measuring electrode, the measurement gas is introduced into the measurement-gas chamber; and (iv) a second electrochemical cell including a second oxygen-ion conductive solid electrolyte body and a pair of electrodes, one of said pair of electrodes is disposed in said measurement-gas chamber while the other of said pair of electrodes is exposed in an external gas space outside the apparatus, said second electrochemical cell performing an oxygen pumping action to feed an oxygen gas from said external gas space into said measurement-gas chamber;

detecting the electromotive force induced between said reference electrode and said measuring electrode of said first electrochemical cell; and determining an amount of a current to be applied between said pair of electrodes of said second electrochemical cell for effecting the oxygen pumping action to be substantially equal to said current to be applied between said reference electrode and said measuring electrode of said first electrochemical cell, so that said electromotive force is proportional to a natural logarithm of the oxygen concentration of the measurement gas introduced into said measurement-gas chamber.

2. A method as defined in claim 1, wherein the oxygen concentration of the measurement gas is calculated from the detected electromotive force, according to the Nernst's equation.

3. An oxygen sensing apparatus for detecting an oxygen concentration of a measurement gas, comprising:

an electrochemical cell including an oxygen-ion conductive solid electrolyte body, a reference electrode exposed to a reference gas having a high concentration of oxygen, and a measuring electrode exposed to the measurement gas, said reference electrode and said measuring electrode are formed on said solid electrolyte body, said electrochemical cell producing an electromotive force corresponding to the oxygen concentration of the measurement gas, due to a difference in the oxygen concentration between the measurement gas and the reference gas;

means for defining a reference-gas chamber formed around said reference electrode, said reference-gas chamber is provided with said reference gas by an oxygen pumping action effected with an amount of current ranging from about 0.1 µA to about 31 µA applied between said reference electrode and said measuring electrode;

a power source for applying a current between said reference electrode and said measuring electrode, to effect said pumping action to provide said reference gas in said reference-gas chamber; and switching means for increasing an amount of said current to be supplied by said power source, with an increase in an expected maximum value of the oxygen concentration of said measurement gas, said expected maximum value defining an upper limit of a measurement range within which said oxygen concentration is determined from said electromotive force.

4. An oxygen sensing apparatus as defined in claim 3, wherein said power source is a variable power source.

5. An oxygen sensing apparatus as defined in claim 3, wherein said means for defining a reference-gas chamber comprises said oxygen-ion conductive solid electrolyte body and a gastight ceramic layer provided on one side of the solid electrolyte body remote from said measuring electrode.

6. An oxygen sensing apparatus as defined in claim 3, wherein said reference-gas chamber is filled with a porous solid electrolyte layer, said reference electrode consisting of a porous electrode which is formed in said porous solid electrolyte layer, in contact with said oxygen-ion conductive solid electrolyte layer.

7. A method of detecting an oxygen concentration of a measurement gas, by using an oxygen sensing apparatus including an electrochemical cell having an oxygen-ion conductive solid electrolyte body, a reference electrode exposed to a reference gas having a high concentration of oxygen, a measuring electrode exposed to the measurement gas, and a reference-gas chamber formed around said reference electrode, said reference electrode and said measuring electrode are formed on said solid electrolyte body, said method comprising the steps of:

applying an amount of current ranging from about 0.1 µA to about 31 µA between said reference electrode and said measuring electrode to effect an oxygen pumping action, to provide said reference gas in said reference-gas chamber;

detecting an electromotive force induced between said reference electrode and said measuring electrode of said electrochemical cell, as an output representative of the oxygen concentration of the measurement gas; and increasing an amount of said current to be applied between said reference electrode and said measuring electrode, with an increase in an expected maximum value of said oxygen concentration of said measurement gas, said expected maximum value defining an upper limit of a measurement range within which said oxygen concentration is determined from said electromotive force.

8. A method as defined in claim 7, wherein said current to be applied between said reference electrode and said measuring electrode is held in a range defined by a lower limit $I_{min}$ (µA) as represented by the formula $I_{min}$ (µA)=0.1 log[$O_2$max]+0.1, and an upper limit $I_{max}$ (µA) as represented by the formula Imax (µA)=5 log[$O_2$max]+1, where $O_2$max (ppm) is said expected maximum value of said oxygen concentration of the measurement gas.

9. A method as defined in claim 7, wherein said current is applied to said electrochemical cell in a direction from said reference electrode to said measuring electrode.

10. A method as defined in claim 7, wherein the oxygen concentration of the measurement gas is calculated from the detected electromotive force, according to the Nernst's equation.

* * * * *